United States Patent [19]

Hsiung

[11] 4,419,509

[45] Dec. 6, 1983

[54] PROCESS FOR DE-CYANOETHYLATING BLOCKED NUCLEOTIDES

[75] Inventor: Hansen M. Hsiung, Indianapolis, Ind.

[73] Assignee: Eli Lilly and Company, Indianapolis, Ind.

[21] Appl. No.: 295,421

[22] Filed: Aug. 24, 1981

[51] Int. Cl.$^3$ .................. C07H 15/12; C07H 17/00
[52] U.S. Cl. ................................ 536/27; 536/28; 536/29
[58] Field of Search .................... 536/28, 27, 29

[56] References Cited

U.S. PATENT DOCUMENTS 3,284,440 11/1966 Patchett et al. ............... 536/28
4,310,662 1/1982 Crea ............................. 536/28

OTHER PUBLICATIONS

Adamiak, R. W., Barciszewska, M. Z., Biala, E., Grzeskowiak, K., Kierzek, R., Kraszewski, A., Markiewicz, W. T., and Wiewiorowski, M., *Nucleic Acids Research* 3, 3397–3408, (1976).

Sood, A. K., and Narang, S. A., *Nucleic Acids Research* 4, 2757–2765, (1977).

*Primary Examiner*—Ethel G. Love
*Attorney, Agent, or Firm*—William C. Martens, Jr.; Arthur R. Whale

[57] ABSTRACT

A β-cyanoethyl blocking group is selectively removed from the phosphate moiety of a nucleotide or polynucleotide by treatment with a primary amine having from 3 to 5 carbon atoms.

8 Claims, No Drawings

PROCESS FOR DE-CYANOETHYLATING BLOCKED NUCLEOTIDES

BACKGROUND OF THE INVENTION

With the advent of recombinant DNA methodology and especially in view of its evident commercial applicability, the ability to synthesize oligodeoxyribonucleotides of defined sequences has become increasingly important.

As now is very well recognized, RNA and DNA are polynucleotides referred to as nucleic acids. The polynucleotides, in turn, are composed of monomers (nucleotides). A nucleotide is a phosphate ester of the N-glycoside of a nitrogenous base and consists of a purine or a pyrimidine base, a pentose (D-ribose in RNA or 2'-deoxy-D-ribose in DNA), and a phosphate group.

Four nitrogenous bases are present in both DNA and RNA. The four present in DNA are:

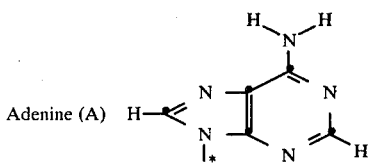

Adenine (A)

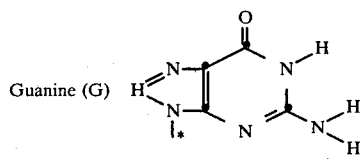

Guanine (G)

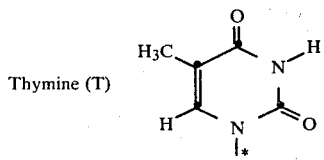

Thymine (T)

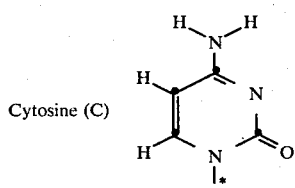

Cytosine (C)

The nitrogenous bases in RNA differ from those in DNA only in that uracil (U) replaces thymine.

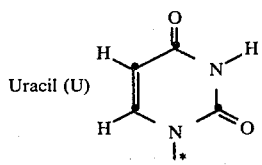

Uracil (U)

The combination of a nitrogenous base at the point of the asterisk (*) in the foregoing formulas with a ribose at its 1'-position is called a ribonucleoside (D-ribose) or a deoxyribonucleoside (2'-deoxy-D-ribose). The corresponding ribonucleotide or deoxyribonucleotide is produced by addition of a phosphate group at the 3'-position of the ribose.

The thus-defined suitably-blocked ribonucleotide or deoxyribonucleotide represents the basic building block in the synthesis of RNA or DNA, respectively. A standard and highly attractive method for synthesizing RNA or DNA is known in the literature as the "triester method". Using the synthesis of a polydeoxyribonucleotide as an example, the procedure involves coupling a mononucleotide or oligonucleotide having a 3'-phosphate diester with a mononucleoside, a blocked 3'-hydroxy oligonucleotide, a mononucleotide, or an oligonucleotide having an available 5'-hydroxyl group. This method can be represented schematically as follows:

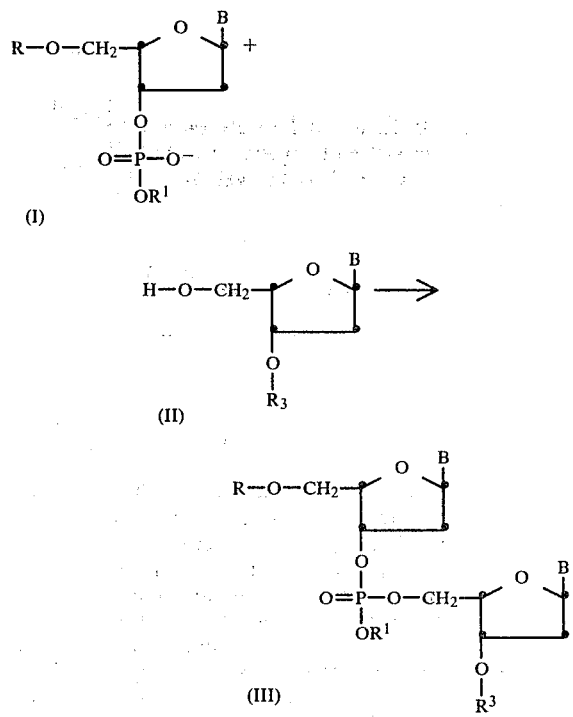

In the foregoing, B is a nitrogenous base selected from adenine, cytosine, guanine, and thymine, each of the first three having their reactive moieties blocked by suitable protecting groups; R is a blocking group for the 5'-hydroxyl; $R^3$ is a blocking group for the 3'-hydroxyl cleavable under alkaline conditions or a group of the formula $$O=\overset{|}{P}-OR^2;$$
$$\underset{OR^1}{|}$$

and $R^1$ and $R^2$ are selectively removable groups which block the reactive phosphate moiety.

Additional discussion of the triester method can be found in various publications including, for example, Narang, S. A., Hsiung, H. M., and Brousseau, R., "Improved Phosphotriester Method for the Synthesis of Gene Fragments", Methods in Enzymology, Vol. 68, Academic Press, New York, New York, (1979), pp. 90-98; and Narang, S. A., Brousseau, R., Hsiung, H. M., and Michniewicz, J. J., "Chemical Synthesis of Deoxyoligonucleotides by the Modified Triester Method", *Methods in Enzymology*, Vol. 65, Academic Press, New York, New York, (1980), pp. 610-620.

The triester method described above, of course, has been applied in coupling two oligonucleotides, an oligonucleotide and a mononucleotide, or, as specifically illustrated above, two mononucleotides. Whatever the entities, the reaction involves the coupling of an available 5'-hydroxyl with a 3'-phosphate diester group. Moreover, the reactant containing the available 5'-hydroxyl can have a blocked terminal phosphate or such can be lacking (i.e., $R^3$ is a 3'-hydroxyl blocking group). The two reactants are coupled in the presence of a solvent, typically pyridine, and in the presence of a coupling agent, for example, 2,4,6-trimethylbenzenesulfonyl tetrazolide.

Whatever the structure of the particular nucleotide reactants, it is essential that the reactant having an available 5'-hydroxyl group be fully blocked at the terminal 3'-phosphate group if such is present. The group $R^2$ appearing in the foregoing formulas represents a blocking group that completes protection of the terminal 3'-phosphate group. If further coupling of the product polynucleotide at its 3'-phosphate site is intended, it is important that the $R^2$ group be one that is removable without disruption of other blocking groups on the molecule.

Customarily, the $R^2$ group of choice is β-cyanoethyl, a group which is selectively removable under mild alkaline conditions. A highly preferred method for selectively removing a β-cyanoethyl group from a nucleotide or oligonucleotide uses anhydrous triethylamine-pyridine. This method is reported in Adamiak, R. W., Barciszewska, M. Z., Biala, E., Grzeskowiak, K., Kierzek, R., Kraszewski, A., Markiewicz, W. T., and Wiewiorowski, M., *Nucleic Acids Research* 3, 3397-3408 (1976), and Sood, A. K., and Narang, S. A., *Nucleic Acids Research* 4, 2757-2765 (1977). Although this method has been highly successful in achieving selective elimination of the β-cyanoethyl blocking group, it suffers from the fact that it is time-consuming, taking 4-6 hours to complete (see Sood et al., supra, p. 2758).

It now has been discovered that the selective removal of a β-cyanoethyl blocking group can be achieved much more rapidly, i.e., in a matter of a few minutes, using a primary amine having from 3 to 5 carbon atoms. It is to such a process that this invention is directed.

SUMMARY OF THE INVENTION

Thus, this invention is directed to a process for selectively removing a β-cyanoethyl blocking group from the phosphate moiety of a nucleotide or polynucleotide, which comprises treating said nucleotide or polynucleotide with a primary amine having from 3 to 5 carbon atoms.

DETAILED DESCRIPTION OF THE INVENTION

As noted, this invention is directed to a process for facilitating selective removal of a β-cyanoethyl blocking group from the phosphate moiety of a nucleotide or polynucleotide.

In any polynucleotide preparation, suitable blocking of otherwise reactive moieties is essential. Thus, certain of the nitrogenous bases require blocking of their reactive amino groups. Typically, adenine and cytosine are benzoylated to protect their free amino groups, and guanine customarily is protected by an isobutyryl group. Thymine, since it has no free amino group, requires no protection. Of course, the foregoing are only examples of suitable blocking groups. Any of a wide range of other blocking groups can be employed.

The group R in the foregoing formulas represents a protecting group for the 5'-hydroxyl moiety. Preferably, the group is labile under mildly acidic conditions. Examples of such groups are tetrahydropyrenyl, 4-methoxytrityl, 4,4'-dimethoxytrityl (DMTr), and the like. 4,4'-Dimethoxytrityl is readily removed in mild acid, for example, 2% benzenesulfonic acid, and represents a preferred protecting group for the 5'-hydroxyl moiety.

The "triester method" is so-called because the coupled product is a phosphate triester. This, in turn, contemplates the use of a nucleotide reactant having a partially-blocked 3'-phosphate group. The group $R^1$ used herein is intended to refer to a group that completes a suitable partial block. This group preferably is one that is removable under alkaline conditions. Examples of suitable groups are phenyl, o-chlorophenyl, 2,4-dichlorophenyl, p-chlorophenyl, p-nitrophenyl, o-nitrophenyl, 2,4-dinitrophenyl, p-mercaptophenyl, and the like. Preferably, $R^1$ is p-chlorophenyl.

A fully blocked nucleotide or the 3'-phosphate-containing terminal of a polynucleotide produced by the triester method contains a blocked phosphate of the formula

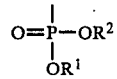

The group $R^2$ represents a group that can be selectively cleaved, generally under mild alkaline conditions and, in accordance with the process of this invention, is β-cyanoethyl. A blocked phosphate in which $R^1$ is p-chlorophenyl and $R^2$ is β-cyanoethyl is conveniently denoted OPCE.

It is also possible that the 3'-terminal of a polynucleotide product lacks a phosphate in which case $R^3$, as hereinbefore described, is a 3'-hydroxyl blocking group cleavable under alkaline conditions. Suitable such groups are acetyl, benzoyl, p-methoxybenzoyl, and chloroacetyl. Preferably, the blocking group is benzoyl (Bz).

Nucleotide coupling is carried out in the presence of a coupling agent. Suitable coupling agents are well recognized by those skilled in the art. Examples of suitable coupling agents are p-nitrobenzenesulfonyl triazolide, benzenesulfonyl triazolide, benzenesulfonyl 4-nitroimidazolide, 2,4,6-triisopropylbenzenesulfonyl 3-nitro-1,2,4-triazolide, 2,4,6-trimethylbenzenesulfonyl 3-nitro-1,2,4-triazolide, 1-(p-toluenesulfonyl) 4-nitroimidazolide, 2,4,6-trimethylbenzenesulfonyl tetrazolide, 2,4,6-triisopropylbenzenesulfonyl chloride, 2,4,6-trimethylbenzenesulfonyl chloride, 2,4,6-triisopropylbenzenesulfonyl tetrazolide, and the like. Preferably, the coupling agent is 2,4,6-triisopropylbenzenesulfonyl tetrazolide or 2,4,6-trimethylbenzenesulfonyl tetrazolide.

The coupling reaction is carried out in the presence of a suitable inert organic solvent under substantially anhydrous conditions. The current solvent of choice is pyridine.

Products produced by nucleotide coupling include polynucleotides having the formula

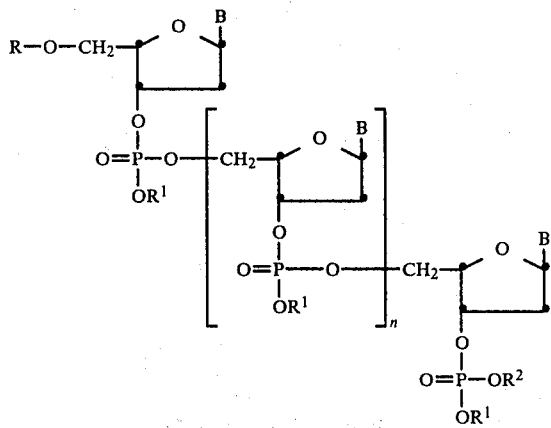

in which B, R, R$^1$, and R$^2$ are as hereinbefore defined and n is zero or an integer up to about 20.

These as well as fully blocked mononucleotides of the formula

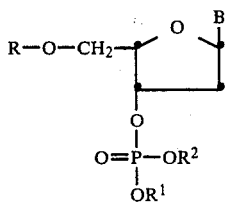

represent the kinds of structures to which the selective deblocking process of this invention may be applied.

In deblocking the β-cyanoethyl (R$^2$) group of a mono- or polynucleotide in accordance with the process of this invention, the mono- or polynucleotide is reacted with a primary amine having from 3 to 5 carbon atoms. Examples of such primary amines are n-propyl amine, n-butyl amine, sec-butyl amine, and t-butyl amine. A hindered amine is highly preferred, and, in particular, t-butyl amine.

Although not essential, the deblocking reaction generally and preferably is carried out in the presence of an inert organic solvent. The current solvent of choice is pyridine.

For the sake of convenience, the decyanoethylation reaction normally is carried out at room temperature. However, any of a wide range of temperatures, generally ranging from about 4° C. to about 30° C. can be employed.

The amount of primary amine used in the process of this invention is directly dependent upon the amount, on a molar basis, of β-cyanoethyl to be cleaved. However, since an excess of the amine can be used without detriment, a large excess, for example, about 10 to about 20 fold, on a molar basis normally will be used.

The progress of the reaction can be monitored using any of a variety of analytical techniques including, for example, thin-layer chromatography (tlc), high performance liquid chromatography (hplc), and the like.

The product, the amine salt of the phosphate diester, can be readily isolated by evaporation of the solvent, any excess amine, and the acrylonitrile byproduct. If desired, the product can be further purified, for example, by recrystallization from a suitable solvent or solvent mixture. The recovered product, with or without further purification, is available for further coupling with a nucleotide or polynucleotide having an available 5'-hydroxyl.

The following examples are provided to further illustrate the process of this invention. They are not intended to be limiting upon the scope thereof.

Example 1—Synthesis of DMTrO-TG-OPCE

5'-O-Dimethoxytritylthymidine-3'-O-p-chlorophenyl-β-cyanoethyl phosphate (1.5 g. 1.9 mmol.) was dissolved in 20 ml. of anhydrous pyridine. t-Butylamine (about 3 ml.) was added dropwise to the above solution with stirring. The reaction was allowed to proceed for about 10 minutes after which decyanoethylation was complete as shown by silica gel thin-layer chromatography (solvent: 10% MeOH/CH$_2$Cl$_2$).

The reaction mixture was evaporated to dryness to remove pyridine, t-butylamine, and acrylonitrile. The dried reaction mixture was then redissolved in CH$_2$Cl$_2$ (20 ml.), and N-isobutyryldeoxyguanosine-3'-O-p-chlorophenyl-β-cyanoethyl phosphate (0.93 g., 1.6 mmol.) was added. The two protected mononucleotides were dried extensively in vacuo and redissolved in 10 ml. of anhydrous pyridine. The condensing agent, 2,4,6-trimethylbenzenesulfonyl tetrazolide (1.01 g., 4 mmol.), was added, and the reaction was allowed to proceed for one hour at ambient temperature. At the end of this period, the coupling reaction was shown to be complete by the disappearance of the 5'-hydroxyl reactant and appearance of an intense trityl positive spot of the dinucleotide (tlc: 10% MeOH/CH$_2$Cl$_2$).

The reaction mixture then was pipetted and transferred to 150 ml. of a 1:1 volume mixture of ether and hexane. A white precipitate containing the dinucleotide product formed and was collected by centrifugation. Thin-layer chromatography (10% MeOH/CH$_2$Cl$_2$) of the supernatant showed no dinucleotide product.

Example 2—Synthesis of DMTrO-GGTA-OPCE

To 200 mg. of DMTrO-GG-OPCE were added approximately 4 ml. of dry pyridine and approximately 2 ml. of t-butyl amine. The decyanoethylation was complete after 10 minutes, as determined by tlc, and the mixture was evaporated to dryness in vacuo. The decyanoethylated dimer was combined with 1.21×10$^{-4}$ moles of HO-TA-OPCE, and the mixture was dried for 30 minutes in vacuo. To initiate coupling, 200 mg. of 2,4,6-trimethylbenzenesulfonyl tetrazolide and approximately 4 ml. of dry pyridine were added. Coupling was complete after one hour. The mixture then was stirred into two centrifuge tubes, each containing 40 ml. of ethy ether. A precipitate of the tetramer formed. The tubes were centrifuged for four minutes, the ether was decanted, and the product was dissolved in dichloromethane, and the solution was evaporated to dryness. After purification on a silica plate in 25% acetone, 70% ethy acetate, b 5% water, 121 mg. (43.2%) of the title compound were recovered.

Example 3—Synthesis of DMTrO-CGGACAGAGACA-OBz

To 56 mg. of DMTrO-CGGA-OPCE were added 2 ml. of pyridine and 1 ml. of t-butyl amine. After 10 minutes the reaction mixture was dried in vacuo. To the residue were added 52 mg. of HO-CAGAGACA-OBz, and the mixture was dried in vacuo for 30 minutes. To the mixture then were added 90 mg. of 2,4,6-trimethylbenzenesulfonyl tetrazolide and 0.5 ml. of dry pyridine. The coupling reaction was completed after one hour. The mixture then was stirred into a centrifuge tube containing 40 ml. of ethyl ether. After centrifuging for four minutes, the ether was decanted, and the product was dissolved in dichloromethane and, the solution was evaporated to dryness. Purification of 5/6 of the material on a silica plate in 25% acetone, 70% ethyl acetate, 5% water gave 40 mg. of the title compound (57.3% yield based upon purification of all of the product).

Example 4—Decyanoethylation of DMTrO-C-OPCE.

5'-O-Dimethoxytrityl-N'-benzoyldeoxycytidine-3'-O-p-chlorophenyl-β-cyanoethyl phosphate (170 mg., 0.2 mmol.) was dissolved in 0.2 ml. of anhydrous pyridine. About 1 ml. of sec-butylamine was added to the solution dropwise. The decyanoethylation was complete in 20 minutes as shown by silica gel chromatography. Excess sec-butylamine and pyridine along with acrylonitrile by-product were removed in vacuo, and the decyanoethylated product was isolated quantitatively.

Example 5—Decyanoethylation of DMTrO-T-OPCE

5'-O-Dimethoxytritylthymidine-3'-O-p-chlorophenyl-β-cyanoethyl phosphate (150 mg., 0.19 mmol.) was dissolved in 2 ml. of anhydrous pyridine. About 1 ml. of n-propylamine was added to the solution. Decyanoethylation was completed after about 2 minutes as shown by tlc (silica gel GF; 10% CH$_3$OH:CH$_2$Cl$_2$). The reaction was quenched immediately by precipitation in a 2:1 mixture of hexane and ether. The resulting mixture was centrifuged, and the supernatant was decanted. The decyanoethylated product was condensed with N-benzoyldeoxyadenosine-3'-p-chlorophenyl-β-cyanoethyl phosphate as in the foregoing examples to produce DMTrO-TA-OPCE.

I claim:

1. A process for selectively removing a β-cyanoethyl blocking group from the phosphate moiety of a nucleotide or polynucleotide, which comprises treating said nucleotide or polynucleotide with a primary amine having from 3 to 5 carbon atoms.

2. Process of claim 1, in which the removal of the β-cyanoethyl group is carried out at a temperature of from about 4° C. to about 30° C.

3. Process of claim 2, in which the removal of the β-cyanoethyl group is carried out at room temperature.

4. Process of claim 2, in which the removal of the β-cyanoethyl group is carried out in the presence of an inert organic solvent.

5. Process of claim 4, in which the removal of the β-cyanoethyl group is carried out in the presence of pyridine.

6. Process of claim 4, in which the primary amine is t-butylamine.

7. Process of claim 4, in which the primary amine is sec-butylamine.

8. Process of claim 4, in which the primary amine is n-propylamine.

* * * * *